(12) United States Patent
Kim et al.

(10) Patent No.: US 11,051,389 B2
(45) Date of Patent: Jun. 29, 2021

(54) ATMOSPHERIC PLASMA DEVICE

(71) Applicant: COBI PLATEC CO., LTD., Seoul (KR)

(72) Inventors: Seong Young Kim, Yongin-si (KR); Shin Duk Kang, Paju-si (KR)

(73) Assignee: COBI PLATEC CO., LTD., Seoul (KR)

( * ) Notice: Subject to any disclaimer, the term of this patent is extended or adjusted under 35 U.S.C. 154(b) by 0 days.

(21) Appl. No.: 16/609,915

(22) PCT Filed: May 14, 2018

(86) PCT No.: PCT/KR2018/005496
§ 371 (c)(1),
(2) Date: Oct. 31, 2019

(87) PCT Pub. No.: WO2018/212527
PCT Pub. Date: Nov. 22, 2018

(65) Prior Publication Data
US 2020/0205277 A1    Jun. 25, 2020

(30) Foreign Application Priority Data
May 16, 2017 (KR) .................... 10-2017-0060330

(51) Int. Cl.
*H05H 1/24* (2006.01)
*A61L 2/14* (2006.01)
(Continued)

(52) U.S. Cl.
CPC ............ *H05H 1/2406* (2013.01); *A61L 2/14* (2013.01); *H01J 37/32348* (2013.01);
(Continued)

(58) Field of Classification Search
CPC .......... H05H 1/00; H05H 1/46; H05H 1/2406; H05H 2001/2414; H05H 2001/2418;
(Continued)

(56) References Cited

U.S. PATENT DOCUMENTS 7,862,564 B2    1/2011 Goble
2007/0072432 A1 *  3/2007 Yoon .................. H05H 1/2406
                                                                    438/707
(Continued)

FOREIGN PATENT DOCUMENTS

JP          5535913 B2      7/2014
JP          2015084290      4/2015
(Continued)

*Primary Examiner* — Henry Luong
(74) *Attorney, Agent, or Firm* — Miles & Stockbridge P.C.

(57) ABSTRACT

The present disclosure relates to a plasma device for alleviation of various skin troubles or for skin care, and provides a remote type plasma device wherein a plasma spray device is separated from the body thereof and is connected to a controller in the body. Plasma is produced under atmospheric pressure at room temperature. The plasma device of the present disclosure includes a dielectric barrier and thus can maintain stable glow discharge. Atmospheric plasma is unexceptionally sprayed through a ground electrode, and thus does not electrically irritate the skin at all.

11 Claims, 6 Drawing Sheets

(51) Int. Cl.
*H01J 37/32* (2006.01)
*H05H 1/46* (2006.01)

(52) U.S. Cl.
CPC .. *H01J 37/32449* (2013.01); *H01J 37/32541* (2013.01); *H01J 37/32825* (2013.01); *H05H 1/46* (2013.01); *H05H 2001/2412* (2013.01); *H05H 2001/2418* (2013.01)

(58) Field of Classification Search
CPC ........ A61L 2/14; A61N 1/44; H01J 37/32348; H01J 37/32449; H01J 37/32541; H01J 37/32825
See application file for complete search history.

(56) References Cited

U.S. PATENT DOCUMENTS

2009/0044661 A1* 2/2009 Li .................... B01J 19/088
 75/10.19
2009/0162263 A1* 6/2009 Chang ............... H01J 37/32825
 422/186.04

FOREIGN PATENT DOCUMENTS

| KR | 20100054368 A | 5/2010 |
| KR | 20100107290 A | 10/2010 |
| KR | 20120039199 A | 4/2012 |
| KR | 101260893 B1 | 5/2013 |
| KR | 101262632 B1 | 5/2013 |
| KR | 20160072759 A | 6/2016 |
| KR | 20170000702 A | 2/2017 |

* cited by examiner

ATMOSPHERIC PLASMA DEVICE

PRIORITY INFORMATION

The present application is a national stage filing under 35 U.S.C. § 371 of PCT/KR2018/005496, filed on May 14, 2018 which claims priority to KR Application No. 10-2017-0060330 filed on May 16, 2017. The applications are incorporated herein by reference in their entirety.

TECHNICAL FIELD

The present invention relates to an atmospheric plasma device for alleviation of various skin troubles or for skin care, and more specifically, to an atmospheric plasma device that is structurally improved to safely and effectively improve skin layers having skin troubles.

BACKGROUND ART

Atmospheric plasma can be applied directly to existing production lines at a pressure of about 1 atm without a separate vacuum device and a reaction chamber, and can be processed through a continuous process.

When using the atmospheric plasma, a conventional DBD (dielectric barrier discharge) technology is widely used. Specifically, when an alternating voltage is applied to a high frequency high voltage electrode in a state in which a dielectric material is inserted between the high frequency high voltage electrode and a ground electrode, gas supplied for plasma formation undergoes electrolytic dissociation and ionization in the electric field region between two electrodes. Thus, the ionized stable plasma may be produced. The produced plasma is composed of not only ions and electrons, but also high-density activating radicals (reactive active species). These radicals are highly reactive so that they easily react with other molecules. For this reason, the reactive active species are effectively used in the processes, such as various skin trouble treatments (skin treatment, disinfection and sterilization), skin cares, cleaning of organic contaminants and surface modifications.

In the case of using a dielectric barrier, since current cannot flow through a dielectric substance in the case of DC power, plasma may be generated by using high frequency AC power. In order to ensure stable plasma generation, an interval between a high frequency high voltage electrode and a ground electrode may be limited, and reaction gas may flow between the two electrodes. Dielectric barrier discharges are sometimes referred to as silent discharges because there are no local waves or noise sparks. The discharge is ignited by power in the form of a sine wave or a pulse.

A dielectric layer blocks reverse current and prevents transition to arc discharge, thereby allowing operation in a continuous mode or a pulse mode.

Meanwhile, in a medical-related technique using plasma, when a skin is irradiated with atmospheric plasma, the rate of blood flow in the skin is increased by energy of atmospheric plasma (ultraviolet rays, mild heat and reactive active species), and elastin and collagen are produced. The resulting elastin and collagen are known to migrate to an epidermal tissue and improve skin wrinkles.

Conventionally, a patent is disclosed in which an ozone generator rubs a skin to activate the skin, thereby improving wrinkles. Since the skin is sterilized and peeled by ozone, cosmetics or nourishing creams are quickly absorbed in the skin, thereby improving the wrinkles.

Recently, an intense pulse light (IPL) treatment system has been widely used in a dermatology for treating skin wrinkles, brown spots and yellowed areas by using light energy generated by applying power to a small arc lamp. This method has the effect of producing elastin and collagen, but it does not play a role of coagulating blood rapidly by increasing the blood flow rate of the wound site, and has the disadvantage of minimizing the effect of ultraviolet rays, which may affect a human body.

As shown in FIG. 1, U.S. Pat. No. 7,862,564 discloses a plasma skin regenerator that assembles a nozzle assembly 16b' which emits a single pulsed plasma to a hand-piece body 16a'. The plasma skin regenerator includes a heat resistant tube 29', an outer electrode 27' disposed outside the heat resistant tube 29', an inner electrode 26' disposed inside the heat resistant tube 29', and a coil 31'. Reaction gas to be dissociated into a plasma state is supplied through a gas path in the heat resistant tube 29', and pulse power having a period of several microseconds is applied between the external electrode 27' and the internal electrode 26' so that a single pulsed plasma stream is ejected from a nozzle 29a'.

However, the skin making contact with the single pulsed plasma produced as described above may be burned by instantaneous high temperature energy. The U.S. Pat. No. 7,862,564 recognizes the above problem and proposes to use the nozzle 29a' by spacing the nozzle 29a' apart from the skin surface by a few mm. In addition, according to an actual user manual, an anesthesia cream has to be applied to the skin in order to eliminate the electrical shock applied to the skin by the single pulsed plasma and the pain felt when the skin is burned.

As shown in FIG. 2, Korean Patent No. 10-1262632 discloses a plasma skin regenerator including an electrode 31' having a Radio Frequency (RF) electrode 311' and a dome-shaped dielectric substance 312', and a counter electrode 32'. The plasma skin regenerator generates plasma by using reaction gas supplied between the RF electrode 311' and the counter electrode 32'.

However, when the RF plasma skin regenerator is brought close to the skin to actually treat the skin, a flow of RF power applied to the dome-shaped RF electrode 311' is generated by the flow of plasma gas, which causes electrons existing in the plasma to flow so that the electrons may be leaked to the skin tissue. Accordingly, the skin may be damaged. Therefore, the patent also discloses that a plasma generating unit has to be spaced apart from the skin by a predetermined distance. In addition, in order to bring the plasma skin regenerator to make contact with the skin, an anesthetic cream has to be applied to the skin.

As shown in FIG. 3, Korean Patent No. 10-1260893 discloses a plasma generator including a generating tube 11' for generating and spraying of plasma using a predetermined gas and a coil tube 12' surrounding a portion of the generating tube 11' to apply a high induced voltage to the generating tube 11'. In addition, a diaphragm 15' having a plurality of spray holes 15a' is disposed at a position slightly spaced apart from a front end of the generating tube 11', so that the plasma sprayed from the front end of the generating tube 11' is sprayed in the form of a plurality of elongated plasmas by passing through the spray holes 15a'.

However, in the above patent, the diaphragm 15' having the spray holes 15a' may serve as a passage for the electric charges, and does not function as a dielectric substance. In other words, the above patent does not relate to the DBD technology.

In addition, because electrons in the thin and sharp plasma have flown out as the plasma gas flows, electrical shock is applied to the skin as in the Korean Patent No. 10-1262632. Accordingly, there is a limitation to prevent the plasma from making direct contact with the skin.

Further, a plasma device disclosed in Korean Unexamined Patent Publication No. 2016-0072759 has a structure of a portable unit that generates plasma between a high frequency high voltage electrode and an atmosphere without supplying reaction gas. In general, the plasma is generated by the high frequency high voltage electrode having at least one surface covered with a dielectric substance and a separate counter electrode facing the dielectric substance. Meanwhile, the plasma device disclosed in Korean Unexamined Patent Publication No. 2016-0072759 does not include a separate counter electrode, and the skin having a resistance of about 1500~2500Ω serves as the counter electrode. That is, the plasma device is provided therein with a high voltage electrode covered with a dielectric substance to which a high frequency pulse voltage is applied and the skin serves as a counter electrode of the high voltage electrode. Specifically, when pulsed power is applied to the high voltage electrode covered with the dielectric substance and an externally exposed dielectric surface is brought close to the skin at an interval of 0.1 to 1 mm, air existing between the skin and the dielectric surface is dissociated into the plasma state by the dielectric barrier discharge and the skin treatment is possible by the plasma.

However, the above patent has a problem that the plasma is not generated when the high frequency high voltage electrode covered with the dielectric substance is spaced apart from the skin by about 2 mm or more. In addition, similar to other patents, anesthetic creams have to be applied to the skin for skin treatment. In general, human body resistance is about 5000Ω, especially, skin resistance is about 2500Ω although it may vary depending on age, sex, environment, frequency, applied voltage, etc. In addition, allowable current of the human body is defined as 0.1 mA in a normal state and 0.5 mA in a single failure state (when one of the power lines is disconnected) according to the IEC601-1 standard. Therefore, when the total current flowing to the skin is 0.1 mA or more, the human body may feel the current, so that it is necessary to apply the anesthetic cream to the skin as described above in order to block the feeling to the current. In addition, the above patent is suggested for the sterilization or skin moisturizing effect rather than the actual skin treatment.

Therefore, there is a need for structural improvement of an atmospheric plasma device to overcome the problems of the related arts and to safely and effectively improve skin layers having various skin problems and to impart skin cosmetic effects.

DETAILED DESCRIPTION OF THE INVENTION

Technical Problem

An object of the present invention is to provide an atmospheric plasma device capable of spraying an atmospheric plasma stably and quickly while effectively improving various skin problems and promoting the skin care.

In addition, another object of the present invention is to provide an atmospheric plasma device which does not cause electrical shock to the skin by spraying both electrons and reactive active species generated by the atmospheric plasma through a plurality of spray holes of a ground electrode.

Technical Solution

In order to achieve the above-described object, according to an aspect of the present invention, there is provided an atmospheric plasma device including: a voltage electrode to which a high frequency power is applied and including a conductor extending in a first direction; a ground electrode facing the voltage electrode and spaced apart from the voltage electrode by a predetermined distance; and a dielectric barrier disposed between the ground electrode and the voltage electrode to shield an end of the voltage electrode, wherein the dielectric barrier and the ground electrode define a space in which an atmospheric plasma is generated and a reaction gas flow path through which a reaction gas is supplied, the ground electrode has a plurality of spray holes for spraying the atmospheric plasma, and at least one of the plurality of spray holes has an off-axis center deviating from a central axis of the voltage electrode.

According to one aspect of the present invention, the voltage electrode may include a rod extending in a first direction and a disk integrally formed with the rod at a front end of the rod, and the dielectric barrier may include a shield plate that shields at least one surface of the disk.

According to one aspect of the present invention, the disk and the shield plate may be disposed substantially perpendicular to the first direction.

According to one aspect of the present invention, the ground electrode may include a housing spaced apart from the dielectric barrier and a ground plate having the plurality of spray holes for spraying the atmospheric plasma.

According to one aspect of the present invention, the plurality of spray holes may have a diameter in a range of 1/20 to 1/3 based on a diameter of the disk.

According to one aspect of the present invention, the shield plate may be in direct contact with the voltage electrode, and the shield plate may be spaced apart from the ground plate by a predetermined distance.

According to one aspect of the present invention, the ground plate may be substantially parallel to the shield plate.

According to one aspect of the present invention, each of the ground plate and the disk may have one of circular, elliptical and polygonal shapes when viewed in a plan view.

According to one aspect of the present invention, the ground plate may be integrally formed with the housing.

According to one aspect of the present invention, the atmospheric plasma device may further include: a high frequency power supply for supplying plasma generation power; and a gas supplier for storing and supplying the reaction gas.

According to one aspect of the present invention, the atmospheric plasma device may further include: a gas pressure regulator; and a gas pressure indicator.

According to one aspect of the present invention, the atmospheric plasma device may further include: a gas flow regulator; and a gas flow indicator.

According to one aspect of the present invention, the atmospheric plasma generated by the reaction gas may be unexceptionally sprayed through the plurality of spray holes.

According to one aspect of the present invention, the voltage electrode may include a rod extending in a first direction and a disk connected to a front end of the rod, the rod may be formed of a non-insulating material provided therein with a power cable, and the disk may be formed of a conductive material.

According to one aspect of the present invention, the dielectric barrier may include a cylindrical body, a shield plate connected to a front end of the body, and a rear shield plate connected to a rear end of the body, and the voltage electrode may extend by passing through the rear shield plate.

Advantageous Effects of the Invention

The atmospheric plasma device according to the present invention provides the following effects.

First, the atmospheric plasma device includes a main body and a plasma spray device, and the main body supplies reaction gas and high frequency power to stably and rapidly spray atmospheric plasma, so that various skin problems can be improved, the skin care can be effectively achieved and the maintenance and repair work can be conveniently performed.

Second, the DBD technology can be applied in order to stably maintain the atmospheric plasma at the room temperature, thereby generating high intensity plasma ranging from a high frequency power to a low power microwave.

Third, a large-capacity atmospheric plasma is formed in a space between ae voltage electrode to which high frequency high voltage is applied and a ground electrode, so that the atmospheric plasma can be intensively and stably sprayed.

Fourth, since a constant distance is maintained between the voltage electrode and the ground electrode and the atmospheric plasma makes contact with the skin by passing through the ground electrode, the plasma device can be used to treat skin troubles without causing electrical shock or damage to the skin.

The above effects are illustrative purposes only and the effects of the present invention will become more apparent from the description for carrying out the invention described below.

BEST MODE

Figure 1:
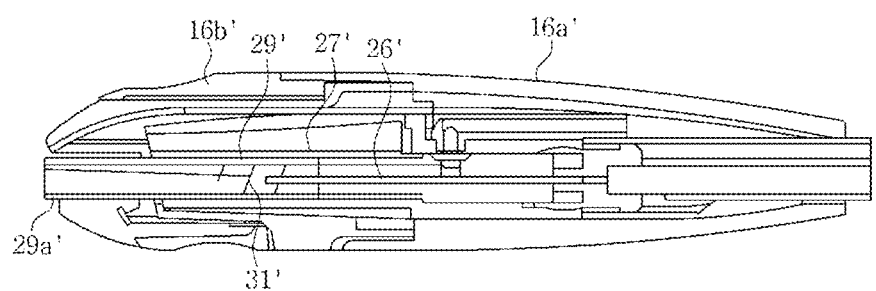
FIG. 1 is a sectional view showing a plasma device of a related art.
Figure 2:
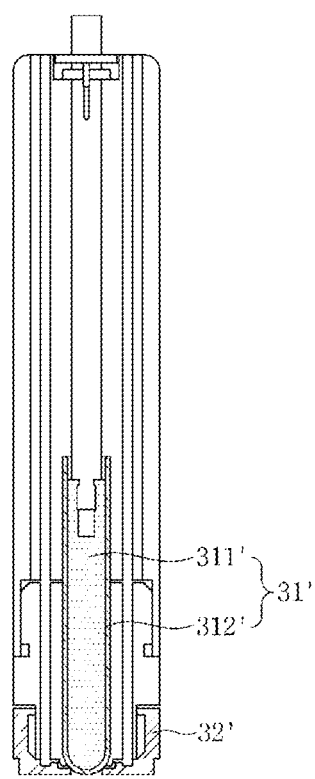
FIG. 2 is a sectional view showing a plasma device of another related art.
Figure 3:
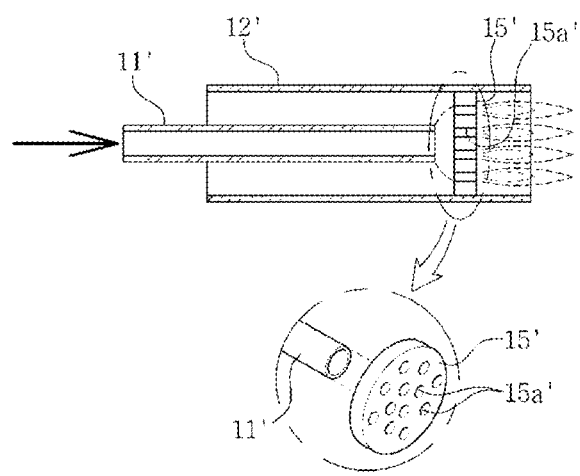
FIG. 3 is a sectional view showing a plasma device of still another related art.

Hereinafter, some embodiments of the present invention will be described in detail with reference to the accompanying drawings. When reference numerals are given to the elements of the drawings, it should be noted that the same components are designated by the same reference numerals as much as possible even though they are shown in different drawings. In describing the embodiments, detailed descriptions of well-known functions and structures incorporated herein may be omitted when they make the subject matter of the embodiments rather unclear.

In describing the components of the embodiments, reference symbols such as first and second may be used. These reference symbols are only for distinguishing the components from other components, and the nature, order or sequence of the components may not be limited by the symbols. In addition, when a part of the specification is referred to as to 'include' or 'comprise' a component, this means that it may further include other components, not to exclude other components unless expressly stated otherwise. In addition, the term 'connection', 'installation' or 'attachment' in the specification does not only mean direct connection, direct installation or direct attachment between components, but also includes indirect connection, indirect installation or indirect attachment, or connection, installation or attachment through other components, and the term should be interpreted as broadly as possible.

Figure 4:
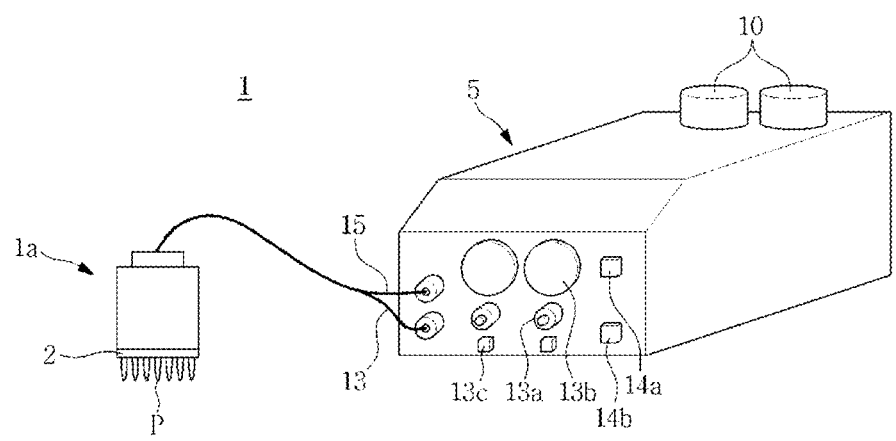
FIG. 4 is a perspective view schematically showing an atmospheric plasma device according to an embodiment of the present invention.
Figure 5A:
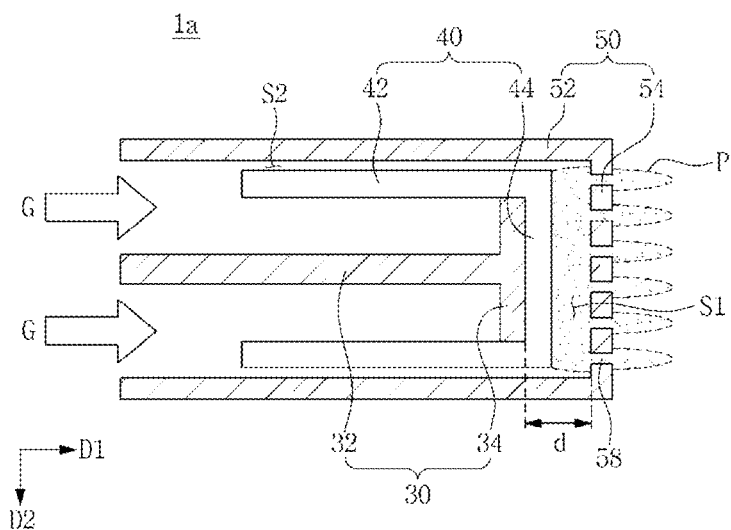
FIG. 5a is a sectional view of a plasma spray device according to an embodiment of the present invention.
Figure 5B:
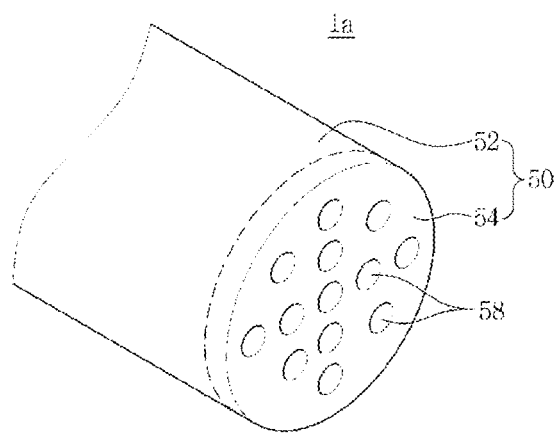
FIG. 5b is a perspective view of the plasma spray device according to an embodiment of the present invention.

FIG. 4 is a perspective view schematically showing an atmospheric plasma device according to an embodiment of the present invention, FIG. 5a is a sectional view of a plasma spray device according to an embodiment of the present invention, and FIG. 5b is a perspective view of the plasma spray device according to an embodiment of the present invention.

Referring to FIGS. 4 to 5b, an atmospheric plasma device 1 according to an embodiment of the present invention includes a plasma spray device 1a and a main body 5. In detail, the plasma spray device 1a and the main body 5 serving as a main controller of the atmospheric plasma device 1 may be separately provided, and connected to each other through a gas supply line 13 and a power supply line 15.

The plasma spray device 1a sprays an atmospheric plasma P through a spray portion 2 formed at a front end of the plasma spray device 1a. For example, the atmospheric plasma P sprayed through the spray portion 2 may be direct sprayed toward the skin to be cured.

The main body 5 may include a high frequency power supply for supplying plasma generating power. When the main body 5 is connected to a commercial power source of 60 Hz and 220 V, an AC power applied by the high frequency power source is converted into high frequency and high voltage power. For this purpose, the high frequency power supply may include an inverter.

In addition, the main body 5 according to an embodiment of the present invention further includes a gas supplier 10 disposed on the main body 5 to store and supply a reaction gas G. The gas supplier 10 may collectively refer to a supplier configured to receive compressed air to generate a high purity reaction gas G. In this case, the reaction gas G may refer to a gas which is supplied between two electrodes of the plasma spray device 1a so as to be transited into a plasma state. The reaction gas G may be an inert gas such as nitrogen, helium, argon, or the like.

For example, when a pair of gas suppliers 10 are provided, nitrogen may be stored in one gas supplier and helium may be stored in the other gas supplier. In this case, the main body 5 may supply one of the two gases to the plasma spray device 1a or supply a mixed gas of the two gases to the plasma spray device 1a as necessary.

The supply of the reaction gas G to the atmospheric plasma device 1 is not essential. For example, the atmospheric plasma device 1 may generate the plasma even under atmospheric conditions without the reaction gas G. However, when the reaction gas G is not supplied, the flow rate of the gas is lower than that of a device to which the reaction gas G is supplied, so it may be difficult to supply the atmospheric plasma P stably and constantly.

The reaction gas G may be supplied from the gas supplier 10 of the main body 5 to the plasma spray device 1a via the gas supply line 13, and the high frequency power may be supplied from the high frequency power supply of the main body 5 to the plasma spray device 1a via the power supply line 15. Although the gas supply line 13 and the power supply line 15 are illustrated as being integrally formed at a portion connected to the plasma spray device 1a, the present invention is not limited thereto, and the gas supply line 13 and the power supply line 15 may be separately formed.

The main body 5 may include a gas pressure regulator 13a, a gas pressure indicator 13b, and a gas selection button 13c. In this case, the number of the gas pressure regulator 13a, the gas pressure indicator 13b, and the gas selection button 13c may correspond to the number of the gas suppliers 10, respectively. For example, the main body 5 according to an embodiment of the present invention may have a pair of gas pressure regulators 13a, a pair of gas pressure indicators 13b, and a pair of gas selection buttons 13c corresponding to the pair of gas suppliers 10. Therefore, a user may appropriately adjust the flow rate of the reaction gas G and the intensity of the atmospheric plasma P by selecting the reaction gas and adjusting the gas pressure, respectively.

Although the main body 5 according to an embodiment of the present invention is described as to include the gas pressure regulator 13a and the gas pressure indicator 13b, the present invention is not limited thereto, and the main body 5 may include a gas flow regulator and a gas flow indicator.

In addition, the main body 5 may further include a main power button 14a and a plasma power button 14b. However, the present invention is not limited thereto, and the plasma power button 14b may be located in the plasma spray device 1a. When the plasma gas button 14b mounted on the main body 5 or the plasma spray device 1a is pressed in a state in which the reaction gas G has been supplied, the power is supplied to a voltage electrode 30 disposed inside the plasma spray device 1a from the main body 5 through the power supply line 15, thereby generating the atmospheric plasma P.

When a skin is irradiated with the atmospheric plasma P several times to several tens of times for a time required for the skin, there is an effect of improving various skin troubles and skin beauty. For example, fine wrinkles and acne of the skin may be improved or eliminated.

The main body 5 of the atmospheric plasma device 1 according to the embodiment of the present invention is separated from the plasma spray device 1a in order to supply the reaction gas and the high frequency power to the plasma spray device 1a and to control the reaction gas. Accordingly, compared to the related art in which the atmospheric plasma device is manufactured as a single product, the atmospheric plasma may be stably and rapidly sprayed at a large capacity, and thus, the atmospheric plasma may effectively improve various skin problems or skin care.

In addition, in the case of changing a method of controlling the atmospheric plasma P such as changing a power supply or replacing a gas, it may be possible to continuously use the plasma spray device 1a by repairing only the main body 5 and the maintenance and repair work may be convenient.

The atmospheric plasma device 1 according to an embodiment of the present invention may be utilized in a professional treatment ship for the skin trouble although the atmospheric plasma device 1 is not portable. In this case, a plurality of plasma spray devices 1a may be connected to one main body 5 in parallel to each other.

Referring to FIG. 5a, the plasma spray device 1a includes a voltage electrode 30, a dielectric barrier 40, and a ground electrode 50. The reaction gas G is supplied to the plasma spray device 1a in an arrow direction and flows inside the plasma spray device 1a.

The voltage electrode 30 may include a rod 32 extending in a first direction D1, which is a longitudinal direction, from the center of the plasma spray device 1a, and a disk 34 integrally formed with the rod 32 at a front end of the rod 32. However, the present invention is not limited thereto, and the rod 32 and the disk 34 may be separately provided and connected to each other.

The disk 34 has a plate shape and may have one of circular, elliptical, and polygonal shapes when viewed in a plan view. For example, in the case where the plasma spray device 1a includes a circular-shaped disk 34, a diameter of the disk 34 may be at least three times larger than a diameter of the rod 32.

The voltage electrode 30 may be formed of iron, aluminum, nickel, tungsten or copper, as is well known to those skilled in the art. That is, each of the rod 32 and the disk 34 may include a conductor formed of the above material. However, the present invention is not limited thereto, and the rod 32 may be formed of a non-insulating material provided therein with a power cable.

The high frequency high voltage may be applied to the voltage electrode 30. In this case, the voltage and the frequency range may be selected to enable the glow discharge at the room temperature.

For example, in the case of a DBD (dielectric barrier discharge) using a helium-nitrogen gas, the high voltage applied to the voltage electrode 30 may have a frequency in the range of 5.0 kHz to 100 kHz in order to maintain a stable atmospheric plasma. Meanwhile, in the case of the DBD using a nitrogen gas, the frequency may be selected from the range of 2.0 kHz to 705 kHz.

For reference, microwave plasma equipment, the performance of which has been proved in recent blood coagulation experiment or sterilization experiment for typical oral bacteria that cause tooth decay, uses low power of less than 10 W in hundreds of MHz to several GHz bands. Particularly, microwaves are required high intensity plasma for effective sterilization. The atmospheric plasma device 1 according to an embodiment of the present invention may generate a microwave plasma similar to the microwave plasma equipment by changing a high frequency power supply.

The dielectric barrier 40 may include a cylindrical body 42 and a shield plate 44 connected to a front end of the body 42. The dielectric barrier 40 may have a substantially "C" shape in which a side into which the reaction gas G flows is opened.

The body 42 and the shield plate 44 may be formed of various ceramics such as alumina or an insulating material such as glass or quartz, and the body 42 and the shield plate 44 may be integrally manufactured.

According to one embodiment of the present invention, the dielectric barrier 40 may be fabricated in a shape complementary to the voltage electrode 30. That is, the dielectric barrier 40 may be configured to have a structure that surrounds the voltage electrode 30 as much as possible.

The shield plate 44 is disposed in contact with one surface of the disk 34 to cover at least one surface of the disk 34, and the body 42 extends from the periphery of the shield plate 44 to surround a considerable part of the rod 32. That is, as shown in FIG. 5*a*, the body 42 may extend in parallel to the rod 32 at a regular interval.

According to the DBD technology, the dielectric barrier 40 is generally attached to either the voltage electrode 30 or the ground electrode 50. However, the plasma spray device 1*a* according to one embodiment of the present invention includes a "C"-shaped dielectric barrier 40, and the shield plate 44 of the dielectric barrier 40 is attached to one side of the disk 34 of the voltage electrode 30 so that the atmospheric plasma P can be concentrated in the front directed to the skin.

The ground electrode 50 may include a cylindrical housing 52 and a ground plate 54 connected to an end of the housing 52.

The housing 52 may surround the voltage electrode 30 and the dielectric barrier 40 and extend in parallel with the body 42 and the rod 32.

The ground plate 54 may include a plurality of spray holes 58 having fine diameters, as shown in FIGS. 5*a* and 5*b*. The plurality of spray holes 58 may have a circular shape.

The housing 52 and the ground plate 54 may be formed of iron, aluminum, nickel, tungsten or copper.

The housing 52 may extend beyond the body 42 and the shield plate 44 along the first direction D1, so that the ground plate 54 may be spaced apart from the shield plate 44 by a predetermined distance. That is, the ground electrode 50 does not make contact with the dielectric barrier 40.

The ground plate 54 may be spaced apart from the disk 34 by a predetermined distance. That is, a predetermined distance d exists between the ground electrode 50 and the voltage electrode 30 in the spray direction of the atmospheric plasma P.

The centers of the plurality of spray holes 58 do not need to necessarily match the central axis of the voltage electrode 30. For example, any one of the plurality of spray holes 58 may be disposed at the center of the ground plate 54 along the central axis of the voltage electrode 30, and other spray holes 58 may be evenly and densely disposed around the one spray hole without matching the central axis of the voltage electrode 30. However, the present invention is not limited thereto, and the plurality of spray holes 58 may be disposed while deviating from the central axis of the voltage electrode 30.

The diameter of each spray hole 58 may be in the range of $1/20$ to $1/3$ based on the diameter of the disk 34. When the diameter of each spray hole 58 exceeds $1/3$ of the diameter of the disk 34, some of the electrons existing in the atmospheric plasma P sprayed from the spray hole 58 may escape to the ground electrode 50, but some electrons may flow toward the adjacent skin, thereby causing the electrical shock to the skin. In addition, the sprayed speed of the atmospheric plasma P may be lowered after passing through the spray holes 58. Meanwhile, when the diameter of each spray hole 58 is less than $1/20$ of the diameter of the disk 34, most of the electrons existing in the atmospheric plasma P may flow toward the ground electrode 50 so that the electrical shock to the skin may not occur. However, the amount of the sprayed atmospheric plasma P is very small so that it is not effective for skin trouble improvement and skin care.

Hereinafter, the operation principle of the atmospheric plasma will be described based on the configuration of the atmospheric plasma device 1 according to one embodiment described above.

First, there are glow discharge, corona discharge, and arc discharge according to the type of plasma. In the case of vacuum direct current discharge, the current-voltage graphs of the glow discharge and the arc discharge are shown in FIG. 6.

Figure 6:
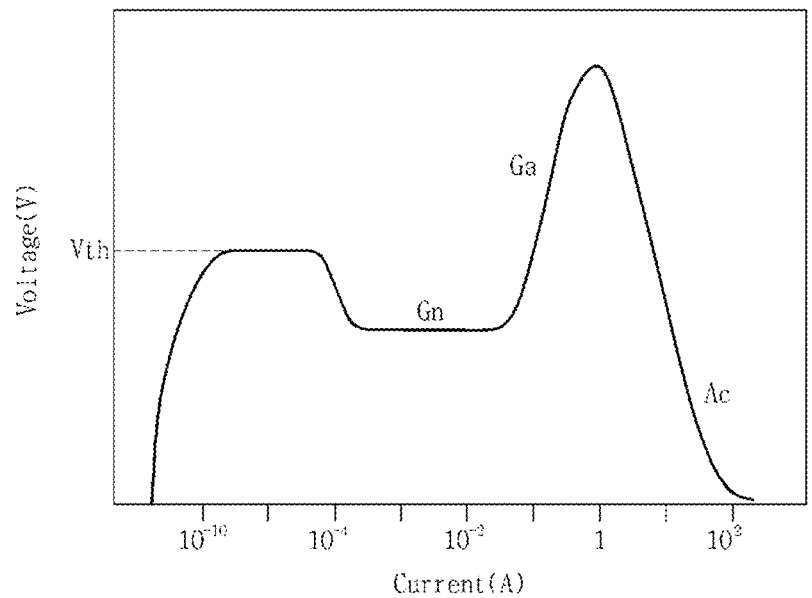
FIG. 6 is a graph of current-voltage relation about glow discharge and arc discharge in vacuum direct current discharge.

Referring to FIG. 6, even when current is extremely small, discharge may start if voltage exceeds a threshold value Vth. After that, in a section where the voltage is kept stable because the voltage decreases slightly and the current increases, stable glow discharge Gn may appear. Thereafter, when the voltage increases rapidly, abnormal glow discharge Ga may occur, and when the current continues to increase, the voltage rapidly decreases and a glow discharge may be transited to the arc discharge period Ac. These abnormal glow discharge Ga may be used in sputtering operations such as vacuum deposition.

Figure 7:
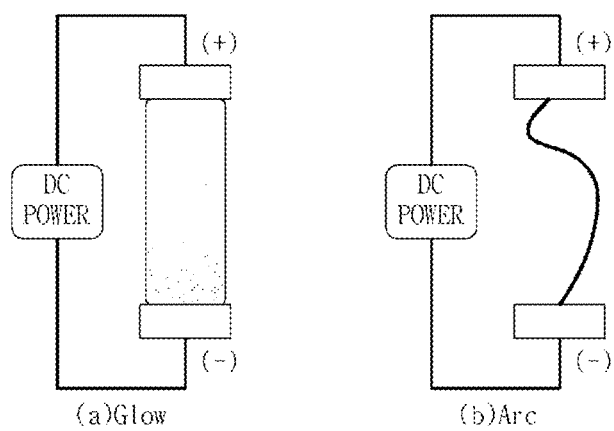
FIG. 7 is a view showing a general discharge form of glow discharge and arc discharge in direct current discharge.

FIG. 7 is a view showing a general discharge form of the glow discharge and the arc discharge in the direct current discharge.

Referring to FIG. 7, in the glow discharge state, the plasma shows a stable flow from a negative electrode (−) to a positive electrode (+), and the density of the plasma on the negative electrode (−) side is relatively higher than that of the positive electrode (+) side. In this state, when the voltage decreases and the current increases, the transition to the arc discharge may occur. In addition, although not shown, the corona discharge is a local discharge form in which a partial discharge occurs between the negative electrode (−) and the positive electrode (+).

However, in the case of the glow discharge, since the positive electrode (+) and the negative electrode (−) are alternately changed when using an AC power source, the density of the plasma is uniformly distributed between the two electrodes without biasing to one of the two electrodes.

In this case, the glow discharge may be prevented from suddenly transitioning to the arc discharge by using the dielectric barrier. This is because electrons are accumulated in the dielectric barrier on the electrode, the accumulated electrons form an electric field opposite to a currently applied electric field at every half cycle of the currently applied electric field, and an opposite magnetic field prevents the conversion from the atmospheric discharge to the arc discharge that often occurs.

The atmospheric plasma device 1 of the present invention may fully utilize the advantage of the glow discharge described above.

Referring again to FIG. 5*a*, when a high frequency high voltage is applied to the voltage electrode 30, a discharge occurs between the voltage electrode 30 and the ground electrode 50. Although the discharge occurs in a space where the voltage electrode 30 and the ground electrode 50 face each other, according to one embodiment of the present invention, a sectional area of the disk 34 in the width direction D2 is wider than that of the rod 32, so that a space 51 between the disk 34 where the high voltage is concentrated and the ground plate 54 opposite to the disk 34 may serve as a main discharge region.

When the supplied reaction gas G flows into a passage S2 provided between the dielectric barrier 40 and the ground electrode 50, the sectional area for passing the reaction gas G may decrease, so that the speed of the reaction gas G may increase. And the, reaction gas G has more high speed to forward. The reaction gas G which has moved forward may be merged in the space between the shield plate 44 and the ground plate 54. In addition, the reaction gas G may be mostly dissociated in the main discharge region 51, and the atmospheric plasma P generated in this region may be sprayed forward through the plurality of spray holes 58.

As the atmospheric plasma P passes through a plurality of spray holes 58 having a small sectional area, the speed of the atmospheric plasma P may increase and thin and elongate atmospheric plasma may be sprayed to the outside.

One of the features of the atmospheric plasma device 1 according to one embodiment of the present invention is that the atmospheric plasma is unexceptionally sprayed through the plurality of spray holes 58, that is, all of the atmospheric plasma P is passed through the ground electrode 50. Accordingly, the electrons in the atmospheric plasma P, which is generated while being dissociated in the discharge region 51, may move toward the adjacent ground electrode 50 and finally exit to the ground, so that current does not flow to the skin adjacent to the ground electrode 50.

In addition, as shown in FIG. 5b, since the plurality of spray holes 58 are densely arranged at the front of the circular ground plate 54, the atmospheric plasma P may be evenly distributed to the skin region facing the ground plate 54.

According to one embodiment of the present invention, a relatively large atmospheric plasma P may be generated by utilizing the space 51 between the shield plate 44 and the ground plate 54, and the generated atmospheric plasma P may be rapidly passed through the plurality of spray holes 58, so that the atmospheric plasma P may be sprayed intensively and stably.

In addition, a predetermined distance d may exist between the disk 34 and the ground plate 54, and all electrons existing in the atmospheric plasma P and finally sprayed to the atmosphere may exit toward the ground by the ground plate 54, so that the current may not be leaked to the skin even though the power applied to the voltage electrode 30 is high and the generated atmospheric plasma P is brought into direct contact with the skin.

When the skin is in close contact with the ground plate 54, the skin may form a ground electrode together with the ground plate 54. In the case of so-called "direct" type where the skin forms a ground electrode, the atmospheric plasma P may be directly sprayed to the skin.

However, according to one embodiment of the present invention, since the atmospheric plasma P makes contact with the skin after all of the atmospheric plasma P has passed through the ground plate 54, there is no atmospheric plasma P directly sprayed toward the skin from the voltage electrode 30, so that the atmospheric plasma P may not cause an electrical shock to the skin or it is not necessary to apply the anesthetic cream to the skin in use.

Hereinafter, an application example of the atmospheric plasma device 1 according to one embodiment of the present invention will be described with reference to the accompanying drawings.

Figure 8:
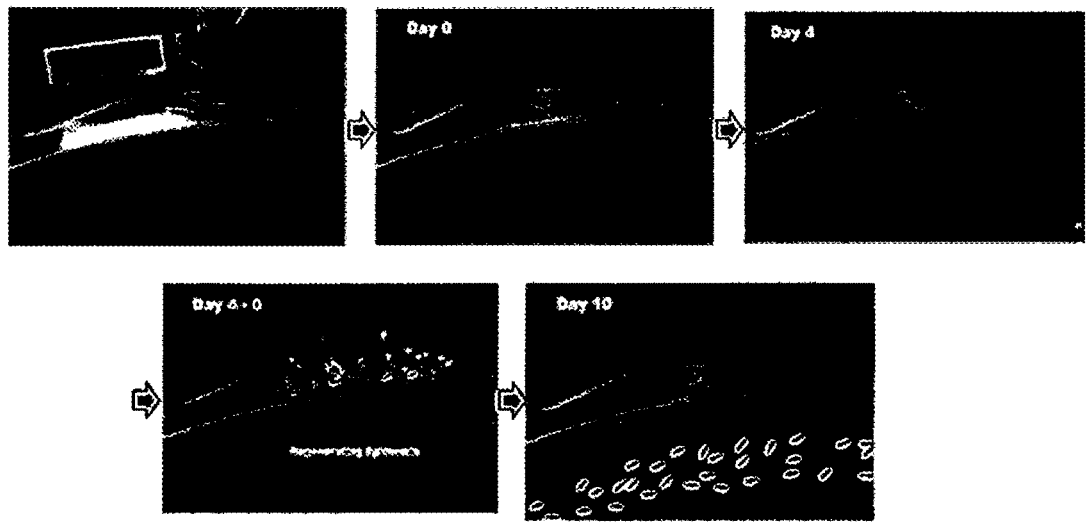
FIG. 8 is a schematic view showing a phenomenon appearing on a skin as time passes when fine wrinkles of the skin are irradiated with an atmospheric plasma by using an atmospheric plasma device according to an embodiment of the present invention.

FIG. 8 is a schematic view showing a phenomenon appearing on a skin as time passes when fine wrinkles of the skin are irradiated with an atmospheric plasma. For the purpose of experiment, the fine wrinkles on the back of the hand were irradiated with the atmospheric plasma for about 1 to 10 minutes at once for 10 days.

Referring to FIG. 8, after about 4 days of irradiation, the skin of the wrinkled area began to peel, and new epithelium was formed, after about 6 days of irradiation, elastin and collagen were formed in the dermis, and after about 10 days of irradiation, the collagen and elastin come out from the dermis and the skin became elastic and wrinkles were improved or eliminated.

Figure 9:
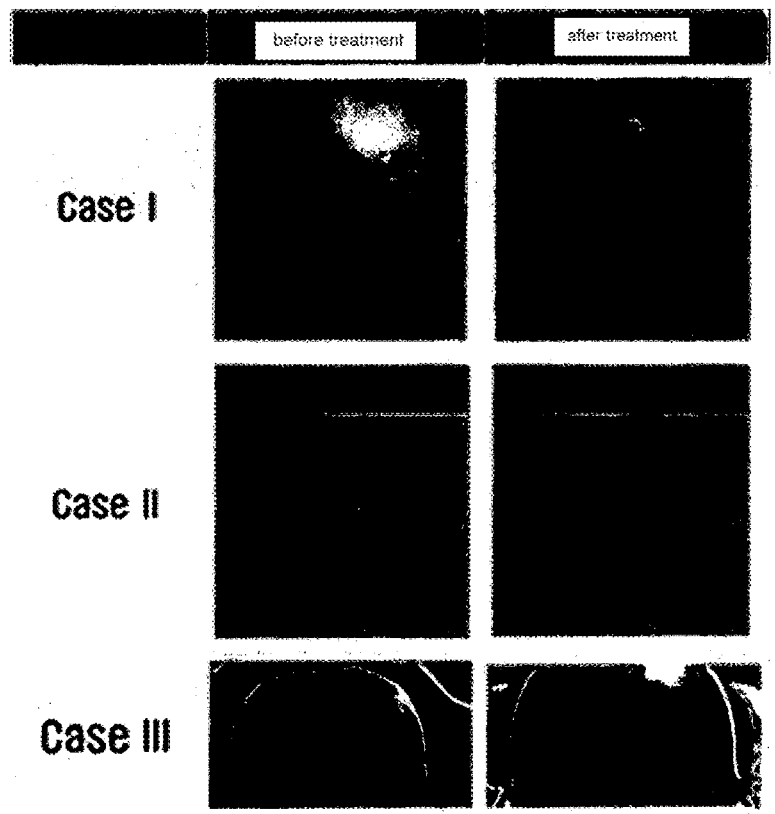
FIG. 9 is a photographic view showing an experimental result obtained by irradiating a site having acne problems with an atmospheric plasma using an atmospheric plasma device according to an embodiment of the present invention.

FIG. 9 is a view showing an experimental result obtained by irradiating a site having acne problems with an atmospheric plasma using an atmospheric plasma device according to the present invention. For the purpose of experiment, the site having acne problems was irradiated with the atmospheric plasma for 1 to 10 minutes at once for total 11 times (11 days, once a day).

Referring to FIG. 9, although there are individual deviations, it can be seen that the acne was significantly improved or eliminated. This is because the bacteria in the purulent site are sterilized or disinfected when the purulent acne site in which the bacteria are present is exposed to the atmospheric plasma P.

As described above, the atmospheric plasma device 1 according to one embodiment of the present invention may improve or eliminate a severe symptom such as fine wrinkles or purulent acne on the skin. In addition, the atmospheric plasma device 1 may also be used to eliminate athlete's foot on nails or toenails, or to improve or eliminate skin inflammation or trouble contaminated with a mold or the like.

Figure 10:
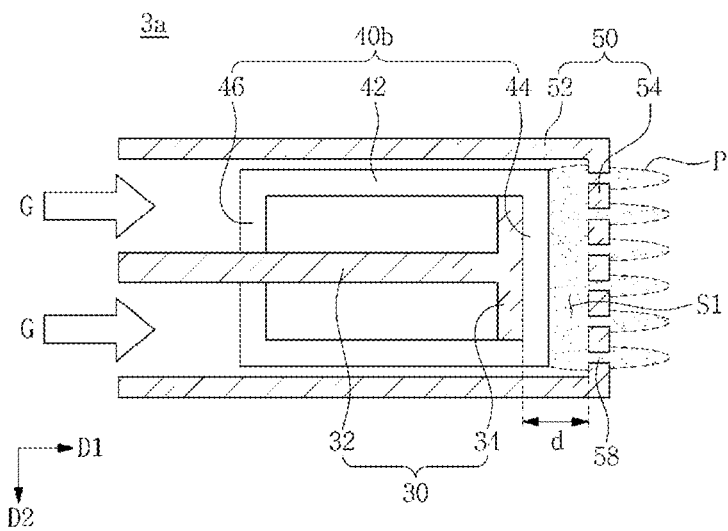
FIG. 10 is a sectional view of a plasma spray device according to another embodiment of the present invention.

FIG. 10 is a sectional view of a plasma spray device according to another embodiment of the present invention.

Referring to FIG. 10, the plasma spray device 3a according to another embodiment of the present invention may further include a rear shield plate 46 connected to a rear end of a body 42 of a dielectric barrier 40b, as compared with the previous embodiment of the present invention. In this case, the dielectric barrier 40b may be configured as a closed rectangular shape to allow the rod 32 to pass through the rear shield plate 46. The rear shield plate 46 may hermetically close the rod 32 or allow a predetermined space with respect to the rod 32.

In this case, since the reaction gas G is not introduced into the empty space between the voltage electrode 30 and the dielectric barrier 40, but quickly introduced through the passage S2, the flow rate of the reaction gas G may be further increased.

In addition, the passage S2 may be expanded by increasing the distance between the body 42 of the dielectric barrier 40 and the housing 52 of the ground electrode 50 so as to increase the flow rate of the reaction gas G.

Figure 11:
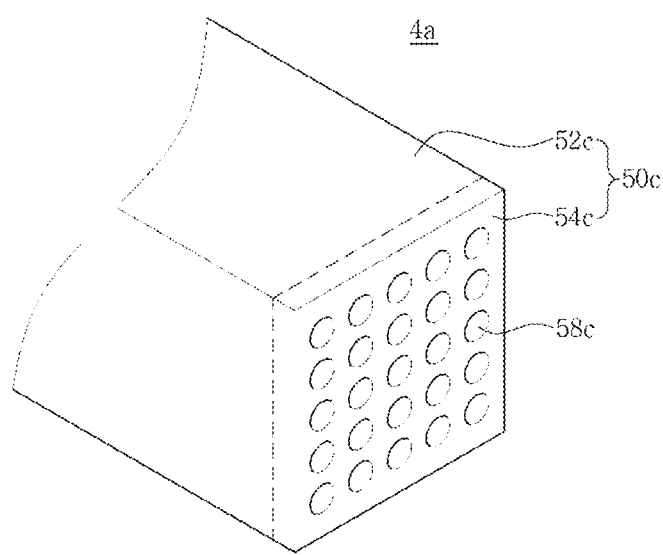
FIG. 11 is a perspective view of a plasma spray device according to another embodiment of the present invention.

FIG. 11 is a perspective view of a plasma spray device according to another embodiment of the present invention.

Referring to FIG. 11, unlike the previous embodiment of the present invention, the plasma spray device 4a according to another embodiment of the present invention may have a rectangular columnar housing 52c and a ground plate 54c having a rectangular plate shape connected to an end of the housing 52c.

In this case, although not shown, the disk disposed in the interior space of the housing 52c and the ground plate 54c may have a rectangular plate shape like the ground plate 54c. However, the present invention is not limited thereto, and the ground plate 54c and the disk may be configured to have various polygonal plate shapes other than the rectangular shape.

The ground plate 54c may include a plurality of spray holes 58c having a very small diameter. As shown in FIG. 12, any one of the plurality of spray holes 58c may be disposed at the center of the ground plate 54c along the central axis of the voltage electrode 30, and other spray holes 58c may be arranged side by side around the one spray hole without matching the central axis of the voltage electrode 30. However, the present invention is not limited thereto, and the plurality of spray holes 58c may be arranged while being offset from adjacent spray holes 58c without matching the central axis of the voltage electrode 30.

Some embodiments of the present invention have been described above with reference to the accompanying drawings, but these embodiments are illustrative purposes only and do not limit the scope of the present invention. Various modifications may be possible by those skilled in the art.

It is to be noted that the shape, size, position, number, and materials of each component or part of the present invention are provided as examples, and may be appropriately changed according to the field of application.

It is apparent that the scope of right of the present invention may extend to the same or similar area as defined in the claims described below.

The invention claimed is:

1. An atmospheric plasma device comprising:
    a voltage electrode to which a high frequency power is applied and including a conductor extending in a first direction;
    a ground electrode facing the voltage electrode and spaced apart from the voltage electrode by a predetermined distance; and
    a dielectric barrier disposed between the ground electrode and the voltage electrode to shield an end of the voltage electrode,
    wherein the dielectric barrier and the ground electrode define a space in which an atmospheric plasma is generated and a reaction gas flow path through which a reaction gas is supplied, the ground electrode has a plurality of spray holes for spraying the atmospheric plasma, and at least one of the plurality of spray holes has a center deviating from a central axis of the voltage electrode,
    wherein the voltage electrode includes a rod extending in the first direction and a disk integrally formed with the rod at a front end of the rod,
wherein the ground electrode includes a cylindrical housing spaced apart from the dielectric barrier and a ground plate having the plurality of spray holes for spraying the atmospheric plasma, and the ground plate is integrally formed with the cylindrical housing,
    wherein the dielectric barrier includes a cylindrical body and a shield plate connected to a front end of the cylindrical body, the cylindrical body is spaced apart from the rod of the voltage electrode and the cylindrical housing of the ground electrode between the rod of the voltage electrode and the cylindrical housing of the ground electrode, the shield plate is in direct contact with the disk of the voltage electrode, and the shield plate is spaced apart from the ground plate by a predetermined distance, wherein the cylindrical housing of the ground electrode surrounds the voltage electrode and the dielectric barrier and the cylindrical housing extends in parallel with the cylindrical body of the dielectric barrier and the rod along the first direction such that a passage for passing the reaction gas is provided between the cylindrical body of the dielectric barrier and the cylindrical housing of the ground electrode and a cross sectional area of the passage is smaller than a sectional area of the shield plate thereby increasing a speed of the reaction gas passing through the passage.

2. The atmospheric plasma device of claim 1, wherein the disk and the shield plate are disposed substantially perpendicular to the first direction.

3. The atmospheric plasma device of claim 1, wherein the plurality of spray holes have a diameter in a range of ⅟₂₀ to ⅓ based on a diameter of the disk.

4. The atmospheric plasma device of claim 1, wherein the ground plate is substantially parallel to the shield plate.

5. The atmospheric plasma device of claim 1, wherein each of the ground plate and the disk has anyone of circular, elliptical and polygonal shapes when viewed in a plan view.

6. The atmospheric plasma device of claim 1, further comprising:
    a high frequency power supply for supplying plasma generation power; and a gas supplier for storing and supplying the reaction gas.

7. The atmospheric plasma device of claim 6, further comprising:
    a gas pressure regulator; and a gas pressure indicator.

8. The atmospheric plasma device of claim 6, further comprising:
    a gas flow regulator; and
    a gas flow indicator.

9. The atmospheric plasma device of claim 1, wherein the atmospheric plasma generated by the reaction gas is sprayed through the plurality of spray holes.

10. The atmospheric plasma device of claim 1, wherein the rod is formed of a non-insulating material provided therein with a power cable, and the disk is formed of a conductive material.

11. The atmospheric plasma device of claim 1, wherein the dielectric barrier includes a cylindrical body, a shield plate connected to a front end of the body, and a rear shield plate connected to a rear end of the body, and the voltage electrode extends by passing through the rear shield plate.

* * * * *